US009192294B2

(12) United States Patent
Sharma et al.

(10) Patent No.: US 9,192,294 B2
(45) Date of Patent: Nov. 24, 2015

(54) SYSTEMS AND METHODS FOR FASTER OPTICAL COHERENCE TOMOGRAPHY ACQUISITION AND PROCESSING

(71) Applicant: Carl Zeiss Meditec, Inc., Dublin, CA (US)

(72) Inventors: Utkarsh Sharma, San Leandro, CA (US); Tilman Schmoll, Dublin, CA (US)

(73) Assignee: CARL ZEISS MEDITEC, INC., Dublin, CA (US)

( * ) Notice: Subject to any disclaimer, the term of this patent is extended or adjusted under 35 U.S.C. 154(b) by 20 days.

(21) Appl. No.: 13/782,873

(22) Filed: Mar. 1, 2013

(65) Prior Publication Data

US 2013/0301000 A1 Nov. 14, 2013

Related U.S. Application Data

(60) Provisional application No. 61/645,516, filed on May 10, 2012, provisional application No. 61/645,450, filed on May 10, 2012.

(51) Int. Cl.
*A61B 3/00* (2006.01)
*A61B 3/14* (2006.01)
(Continued)

(52) U.S. Cl.
CPC ............... *A61B 3/102* (2013.01); *A61B 5/489* (2013.01); *G01B 9/02004* (2013.01); *G01B 9/02007* (2013.01); *G01B 9/02009* (2013.01); *A61B 5/066* (2013.01); *A61B 6/488* (2013.01)

(58) Field of Classification Search
CPC ...... A61B 3/102; A61B 5/0066; A61B 5/489; G01B 9/02004; G01B 9/02007; G01B 9/02044; G01B 9/02091; G01B 9/02087; G06T 2207/30041

USPC ......... 351/208, 215, 221, 246, 206, 205, 209; 356/479, 497; 382/116, 107, 128, 131; 600/504, 160, 425, 558

See application file for complete search history.

(56) References Cited

U.S. PATENT DOCUMENTS 5,321,501 A 6/1994 Swanson et al.
5,459,570 A 10/1995 Swanson et al.
(Continued)

FOREIGN PATENT DOCUMENTS

WO 2010/006785 A1 1/2010
WO 2011/037980 A2 3/2011

OTHER PUBLICATIONS

Non-Final Office Action received for U.S. Appl. No. 12/611,994, mailed on Apr. 14, 2011, 14 pages.
(Continued)

*Primary Examiner* — Scott J Sugarman
*Assistant Examiner* — Collin X Beatty
(74) *Attorney, Agent, or Firm* — Morrison & Foerster LLP

(57) ABSTRACT

Systems and methods for faster acquisition and processing of OCT image data are presented. In one embodiment of the present invention, an OCT system is operated in two different acquisition modes of different axial resolutions to allow for efficient collection of OCT Angiography data while also collecting high resolution OCT data. In another embodiment, a reduced subset of a collected data set is used for OCT Angiography data analysis. In another embodiment, a sweep of a swept-source laser is split into different spectral components covering different transverse locations on the sample. A further aspect includes the ability to process all or a portion of collected OCT data with one motion contrast technique before or while a second set is processed using a different motion contrast technique.

17 Claims, 4 Drawing Sheets

(51) Int. Cl.
*A61B 3/10* (2006.01)
*G01B 9/02* (2006.01)
*A61B 5/00* (2006.01)
*A61B 6/00* (2006.01)
*A61B 5/06* (2006.01)

(56) References Cited

U.S. PATENT DOCUMENTS

| | | | |
|---|---|---|---|
| 5,506,634 | A | 4/1996 | Wei et al. |
| 5,975,697 | A | 11/1999 | Podoleanu et al. |
| 6,549,801 | B1 | 4/2003 | Chen et al. |
| 6,769,769 | B2 | 8/2004 | Podoleanu et al. |
| 6,985,235 | B2 | 1/2006 | Bao et al. |
| 7,301,644 | B2 | 11/2007 | Knighton et al. |
| 7,330,270 | B2 | 2/2008 | O'Hara et al. |
| 7,342,659 | B2 | 3/2008 | Horn et al. |
| 7,359,062 | B2 | 4/2008 | Chen et al. |
| 7,375,818 | B2 | 5/2008 | Kawahara |
| 7,382,464 | B2 | 6/2008 | Everett et al. |
| 7,414,779 | B2 | 8/2008 | Huber et al. |
| 7,415,049 | B2 | 8/2008 | Flanders et al. |
| 7,505,142 | B2 | 3/2009 | Knighton et al. |
| 7,602,500 | B2 | 10/2009 | Izatt et al. |
| 7,692,797 | B2 | 4/2010 | Kawahara |
| 7,768,651 | B2 | 8/2010 | Ueno et al. |
| 7,864,335 | B2 | 1/2011 | Terakawa et al. |
| 7,884,945 | B2 | 2/2011 | Srinivasan et al. |
| 7,995,814 | B2 | 8/2011 | Fingler et al. |
| 2005/0171438 | A1* | 8/2005 | Chen et al. ............. 600/476 |
| 2005/0190371 | A1 | 9/2005 | Knuttel |
| 2006/0066869 | A1 | 3/2006 | Ueno et al. |
| 2006/0164653 | A1 | 7/2006 | Everett et al. |
| 2007/0024856 | A1 | 2/2007 | Izatt et al. |
| 2007/0216909 | A1 | 9/2007 | Everett et al. |
| 2007/0276269 | A1 | 11/2007 | Yun et al. |
| 2008/0025570 | A1* | 1/2008 | Fingler et al. ............ 382/107 |
| 2008/0273783 | A1 | 11/2008 | Toth et al. |
| 2008/0309881 | A1* | 12/2008 | Huang et al. ............. 351/246 |
| 2009/0046295 | A1 | 2/2009 | Kemp et al. |
| 2009/0153874 | A1* | 6/2009 | Rogers et al. ............ 356/497 |
| 2009/0270738 | A1* | 10/2009 | Izatt et al. ............... 600/476 |
| 2010/0110376 | A1* | 5/2010 | Everett et al. ............ 351/206 |
| 2010/0150422 | A1 | 6/2010 | Vakoc et al. |
| 2010/0278402 | A1* | 11/2010 | Everett et al. ............ 382/128 |
| 2010/0280315 | A1* | 11/2010 | Pan ......................... 600/109 |
| 2011/0009701 | A1* | 1/2011 | Feldman et al. .......... 600/178 |
| 2011/0102802 | A1* | 5/2011 | Izatt et al. ............... 356/479 |
| 2011/0170111 | A1* | 7/2011 | Rolland et al. ........... 356/479 |
| 2011/0176142 | A1* | 7/2011 | Hacker et al. ............ 356/479 |
| 2011/0282181 | A1* | 11/2011 | Wang et al. .............. 600/407 |
| 2011/0301455 | A1* | 12/2011 | Numajiri et al. .......... 600/425 |
| 2012/0004562 | A1* | 1/2012 | Fingler et al. ............ 600/504 |
| 2012/0008146 | A1* | 1/2012 | Tearney et al. ........... 356/479 |
| 2012/0026463 | A1* | 2/2012 | Makihira et al. .......... 351/206 |
| 2012/0026464 | A1* | 2/2012 | Berger et al. ............. 351/206 |
| 2012/0188555 | A1 | 7/2012 | Izatt et al. |
| 2012/0277579 | A1 | 11/2012 | Sharma et al. |
| 2013/0120757 | A1 | 5/2013 | Yu et al. |

OTHER PUBLICATIONS

Final Office Action received for U.S. Appl. No. 12/611,994, mailed on Oct. 3, 2011, 13 pages.
Notice of Allowance received for U.S. Appl. No. 12/611,994, mailed on Dec. 22, 2011, 8 pages.
Non Final Office Action received for U.S. Appl. No. 12/611,994, mailed on Oct. 18, 2012, 13 pages.
Notice of Allowance received for U.S. Appl. No. 12/611,994, mailed on Feb. 22, 2013, 8 pages.
Fujimoto, James G., "Optical Coherence Tomography for Ultrahigh Resolution in Vivo Imaging", Nature Biotechnology, vol. 21, No. 11, Nov. 2003, pp. 1361-1367.
Fujimoto et al., "Optical Coherence Tomography: An Emerging Technology for Biomedical Imaging and Optical Biopsy", Neoplasia, vol. 2, No. 1-2, Jan.-Apr. 2000, pp. 9-25.

Fercher et al., "Optical Coherence Tomography-Principles and Applications", Reports on Progress in Physics, vol. 66, 2003, pp. 239-303.
Huang et al., "Optical Coherence Tomography", Science, vol. 254, Nov. 22, 1991, pp. 1178-1181.
Leitgeb et al., "Spectral Measurement of Absorption by Spectroscopic Frequency-domain Optical Coherence Tomography", Optics Letters, vol. 25, No. 11, Jun. 1, 2000, pp. 820-822.
Leitgeb et al., "Performance of Fourier Domain vs. Time Domain Optical Coherence Tomography", Optics Express vol. 11, No. 8, Apr. 21, 2003, pp. 889-894.
Považay et al., "High-Speed High-Resolution Optical Coherence Tomography at 800 and 1060 nm", Proceedings of the SPIE, vol. 7139, 2008, 6 pages.
Rollins et al., "Emerging Clinical Applications of Optical Coherence Tomography", Optics and Photonics News, vol. 13, No. 4, Apr. 2002, pp. 36-41.
Schmitt, Joseph M., "Optical Coherence Tomography (OCT): A Review", IEEE Journal of Selected Topics in Quantum Electronics, vol. 5, No. 4, Jul./Aug. 1999, pp. 1205-1215.
Non-Final Office Action received for U.S. Appl. No. 13/354,066, mailed on Feb. 27, 2014, 12 pages.
Notice of Allowance received for U.S. Appl. No. 13/903,797, mailed on Feb. 12, 2014, 7 pages.
Barfuss et al., "Modified Optical Frequency Domain Reflectometry with High Spatial Resolution for Components of Integrated Optic Systems", Journal of Lightwave Technology, vol. 7, No. 1, Jan. 1989, pp. 3-10.
Choma et al., "Sensitivity Advantage of Swept Source and Fourier Domain Optical Coherence Tomography", Optics Express, vol. 11, No. 18, Sep. 8, 2003, pp. 2183-2189.
Eickhoff et al., "Optical Frequency Domain Reflectometry in Single-Mode Fiber", Appl. Phys. Lett, vol. 39, No. 9, Nov. 1, 1981, pp. 693-695.
Golubovic et al., "Optical Frequency-Domain Reflectometry using Rapid Wavelength Tuning of a Cr4+:Forsterite Laser", Optics Letters, vol. 22, No. 22, Nov. 15, 1997, pp. 1704-1706.
Gora et al., "Ultra High-Speed Swept Source OCT Imaging of the Anterior Segment of Human Eye at 200 kHz with Adjustable Imaging Range", Optics Express, vol. 17, No. 17, Aug. 17, 2009, pp. 14880-14894.
Huber et al., "Amplified, Frequency Swept Lasers for Frequency Domain Reflectometry and OCT Imaging: Design and Scaling Principles", Optics Express, vol. 13, No. 9, May 2, 2005, pp. 3513-3528.
Kourogi et al., "Programmable High Speed (~1MHz) Vernier-Mode-Locked Frequency-Swept Laser for OCT Imaging", Proc. of SPIE, vol. 6847, 2008, pp. 68470Z-1-68470Z-8.
Lee et al., "Wide Tuning Range Wavelength-Swept Laser with a Single SOA at 1020 nm for Ultrahigh Resolution Fourier-Domain Optical Coherence Tomography", Optics Express, vol. 19, No. 22, Oct. 24, 2011, pp. 21227-21237.
Lee, Sang-Won, "Optimization for Axial Resolution, Depth Range, and Sensitivity of Spectral Domain Optical Coherence Tomography at 1.3 µm", Journal of the Korean Physical Society, vol. 55, No. 6, Dec. 2009, pp. 2354-2360.
Lexer et al., "Wavelength-Tuning Interferometry of Intraocular Distances", Applied Optics, vol. 36, No. 25, Sep. 1, 1997, pp. 6548-6553.
International Search Report and Written Opinion received for PCT Patent Application No. PCT/EP2012/050796, mailed on Apr. 27, 2012, 11 pages.
Xi et al., "Evaluation of Spectrometric Parameters in Spectral-Domain Optical Coherence Tomography", Applied Optics, vol. 50, No. 3, Jan. 20, 2011, pp. 366-372.
Xi et al., "Generic Real-time Uniform K-space Sampling Method for High-Speed Swept-Source Optical Coherence Tomography", Optics Express, vol. 18, No. 9, Apr. 26, 2010, pp. 9511-9517.
Yasuno et al., "Three-Dimensional and High-Speed Swept-Source Optical Coherence Tomography for in Vivo Investigation of Human Anterior Eye Segments", Optics Express, vol. 13, No. 26, Dec. 26, 2005, pp. 10652-10664.
Yun et al., "Motion Artifacts in Optical Coherence Tomography with Frequency-Domain Ranging", Optics Express, vol. 12, No. 13, Jun. 28, 2004, pp. 2977-2998.

(56) References Cited

OTHER PUBLICATIONS

Yun et al., "High-Speed Optical Frequency Domain Imaging", Optics Express, vol. 11, No. 22, Nov. 3, 2003, pp. 2953-2963.
Yun et al., "Removing the Depth-Degeneracy in Optical Frequency Domain Imaging with Frequency Shifting", Optics Express, vol. 12, No. 20, Oct. 4, 2004, pp. 4822-4828.
An et al., "In vivo Volumetric Imaging of Vascular Perfusion within Human Retina and Choroids with Optical Micro-Angiography", Optics Express, vol. 16, No. 15, Jul. 21, 2008, pp. 11438-11452.
Blatter et al., "Ultrahigh-Speed Non-Invasive Widefield Angiography", Journal of Biomedical Optics, vol. 17, No. 7, Jul. 2012, pp. 070505-1-070505-3.
Fingler et al., "Mobility and Transverse Flow Visualization using Phase Variance Contrast with Spectral Domain Optical Coherence Tomography", Optics Express, vol. 15, No. 20, Oct. 1, 2007, pp. 12636-12653.
Fingler et al., "Volumetric Microvascular Imaging of Human Retina using Optical Coherence Tomography with a Novel Motion Contrast Technique", Optics Express, vol. 17, No. 24, Nov. 23, 2009, pp. 22190-22200.
Jia et al., "Split-Spectrum Amplitude-Decorrelation Angiography with Optical Coherence Tomography", Optics Express, vol. 20, No. 4, Feb. 13, 2012, pp. 4710-4725.
Kim et al., "In vivo Volumetric Imaging of Human Retinal Circulation with Phase-Variance Optical Coherence Tomography", Biomedical Optics Express, vol. 2, No. 6, Jun. 1, 2011, pp. 1504-1513.
Klein et al., "Multi-MHz FDML OCT: Snapshot Retinal Imaging at 6.7 Million Axial-Scans Per Second", Proc. of SPIE, vol. 8213, 2012, pp. 82131E-1-82131E-6.
Lee et al., "In vivo Optical Frequency Domain Imaging of Human Retina and Choroid", Optics Express, vol. 14, No. 10, May 15, 2006, pp. 4403-4411.
Leitgeb et al., "Ultrahigh Resolution Fourier Domain Optical Coherence Tomography", Optics Express, vol. 12, No. 10, May 17, 2004, pp. 2156-2165.
Makita et al., "Optical Coherence Angiography", Optics Express, vol. 14, No. 17, Aug. 21, 2006, pp. 7821-7840.
Mariampillai et al., "Optimized Speckle Variance OCT Imaging of Microvasculature", Optics Letters, vol. 35, No. 8, Apr. 15, 2010, pp. 1257-1259.
Podoleanu et al., "OCT En-Face Images from the Retina with Adjustable Depth Resolution in Real Time", IEEE Journal of Selected Topics in Quantum Electronics, vol. 5, No. 4, Jul./Aug. 1999, pp. 1176-1184.
Wang et al., "Three Dimensional Optical Angiography", Optics Express, vol. 15, No. 7, Apr. 2, 2007, pp. 4083-4097.
Wojtkowski et al., "Three-Dimensional Retinal Imaging with High-Speed Ultrahigh-Resolution Optical Coherence Tomography", Ophthalmology, vol. 112, No. 10, Oct. 2005, pp. 1734-1746.
Zhang et al., "Swept Laser Source at 1 µm for Fourier Domain Optical Coherence Tomography", Applied Physics Letters, vol. 89, 2006, pp. 073901-1-073901-3.
Non-Final Office Action received for U.S. Appl. No. 13/903,797, mailed on Sep. 6, 2013, 14 pages.
Non-Final Office Action received for U.S. Appl. No. 13/795,953, mailed on Oct. 21, 2014, 9 pages.

* cited by examiner

SYSTEMS AND METHODS FOR FASTER OPTICAL COHERENCE TOMOGRAPHY ACQUISITION AND PROCESSING

PRIORITY

The following application claims priority to U.S. Provisional Application Ser. Nos. 61/645,516 filed May 10, 2012 and 61/645,450 filed May 10, 2012, the contents of both of which are hereby incorporated by reference.

TECHNICAL FIELD

This invention relates to optical imaging. In particular, the invention provides systems and methods to increase the speed in collecting and/or processing optical coherence tomography (OCT) imaging data for various types of imaging and measurements.

BACKGROUND

Optical coherence tomography (OCT) is a noninvasive, noncontact imaging modality that uses coherence gating to obtain high-resolution cross-sectional images of tissue microstructure. In Fourier domain OCT (FD-OCT), the interferometric signal between light from a reference and the back-scattered light from a sample point is recorded in the frequency domain rather than the time domain. After a wavelength calibration, a one-dimensional Fourier transform is taken to obtain an A-line spatial distribution of the object scattering potential. The spectral information discrimination in FD-OCT can be accomplished by using a dispersive spectrometer in the detection arm in the case of spectral-domain OCT (SD-OCT) or rapidly tuning a swept laser source in the case of swept-source OCT (SS-OCT).

The axial or depth resolution of the FD-OCT system is determined by the actual spectral width recorded and used for reconstruction. The axial range over which an OCT image is taken (imaging depth, scan depth or imaging range) is determined by the sampling interval or resolution of the optical frequencies recorded by the OCT system. Specifically, in SD-OCT, the spectrometer disperses different wavelengths to the detector elements. The resolution of the optical frequencies and therefore the imaging depth depends on the width of the portion of the spectrum that is measured by a single detector element or pixel.

In some SS-OCT implementations, the swept-source tunes or sweeps the wavelength of the source over time. In this case, the resolution of the optical frequencies depends on a spectral separation of the measuring light at adjacent points in time. The spectral resolution of the measurements will increase with sampling density unless it is limited by the instantaneous linewidth of the laser. For most of the swept-sources, OCT signals acquired with adjacent points separated by uniform (constant) time intervals result in a non-uniform sample distribution in k (wave vector) space. Normally, these optical frequencies are further numerically re-sampled (or interpolated) to get equally k-spaced samples before the Fourier transform is actually taken. This will digitally affect the actual imaging depth in the OCT reconstruction as the imaging depth is now determined by the resolution in wave-numbers (K). In other implementations, Fabry-Pérot interferometers (FPI or etalon) (see for example Zhang et al "Swept laser source at 1 um for Fourier domain optical coherence tomography," Applied Physics Letters 89, 073901 2006) and Mach-Zehnder interferometers (see for example Xi et al "Generic real-time uniform k-space sampling method for high-speed swept-source optical coherence tomography," Optics Express 18(9):9511 2010) can be used to generate external clock signals with uniform k-spacing. In this case, the digitizer (or data acquisition system) of the SS-OCT system is running in an "external clock" mode, whereby it takes the external k-clock signals for point by point sampling.

There are several types of OCT measurements which require particularly dense spatial sampling, but may tolerate relatively low axial resolution. Such measurements include but are not limited to, OCT Angiography methods (e.g. Doppler OCT, phase contrast, phase variance, speckle variance, power of Doppler shift, normalized vector difference, ultrahigh sensitive optical microangiography (UHS-OMAG)), photoreceptor imaging, wide-field anterior segment scans, wide field overview scans. For example, OCT Angiography or OCT photoreceptor images are often displayed as 2D projection images. While a high transverse sampling is required to reduce phase noise in the case of OCT Angiography, or support a high lateral resolution in the case of photoreceptor imaging, the axial resolution is less relevant, because the processed data is only displayed in projected or enface 2D images. OCT Angiography methods typically require an over sampling of about 4-12 samples per transverse position. This increases the acquisition time by the same factor. This is problematic as increased acquisition time directly affects image quality as well as patient comfort. It is desirable to collect data over as large a field of view as possible which also involves acquisition time, patient comfort and motion considerations.

One of the approaches to solve this problem is to use very high speed OCT systems (See for example Klein et al. "The effect of micro-saccades on the image quality of ultrawidefield multimegahertz OCT data," SPIE Photonices West 2012, Paper #8209-13 (2012) or Blatter et al. "Ultrahigh-speed non-invasive widefield angiography," J. Biomed. Opt. 17, 070505, 2012 hereby incorporated by reference), however, such systems can be very complex and costly. Also, the high speed systems would require faster detection electronics and would result in large numbers of data sets that could further slowdown the analysis of the data. Additional approaches to overcome the problems include the use of tracking, and montaging of multiple data sets.

SUMMARY

In light of the limitations in the prior art described above, the present invention is directed towards systems and methods for changing the acquisition and processing speeds for OCT imaging for particular types of OCT data to enable fast display of one image from the data while data for another image is being collected or processed. In OCT angiography, high axial resolution is not very useful for improving the quality of en face vasculature images because the majority of blood-flow contrast OCT techniques have posterior shadow artifacts below the blood vessel, thereby effectively degrading the axial resolution for motion-contrast signals (see for example Kim et al. "In vivo volumetric imaging of human retinal circulation with phase-variance OCT," Biomedical Optical Express, 2, 1504-1513 (2011)). In addition, typical representation of OCT angiography data is through display of summed en face images from motion contrast 3D volumes that further reduce the need for high axial resolution. This fact makes it possible to trade-off between axial resolution and acquisition or processing speed without any significant impact on the results of the analysis or en face image quality. Embodiments of the current invention use this fact to purposely degrade the axial resolution of the OCT angiography or motion contrast image in order to increase the acquisition speed or processing time without any significant effect on the en face image quality. It is then possible to operate the system in two modes of different axial resolutions, one for generating OCT angiography or survey en face images on a rapid time basis and the other for generating high axial resolution images. These high resolution images could be either OCT structural images or additional OCT Angiography images.

The advantages of this method for applications in OCT angiography are twofold:
1. Capability of increasing the acquisition speed for OCT angiography without any significant impact on en face vasculature image quality.
2. Capabilities of generating larger FOV en face images of vasculature at reduced post processing effort.

In one embodiment of the present invention, the resolution switch is accomplished during data acquisition, where the system is controlled to collect data at two different axial resolutions. A swept-source OCT (SS-OCT) system can be used where the laser source has a configurable tuning bandwidth that is inversely proportional to the sweep rate. For certain fast angiography modes, the laser could operate at much higher A-scan rates at the cost of lower wavelength bandwidths (lower axial resolutions). An alternative embodiment of the invention in which the data is processed in two separate batches, one consisting of a smaller spectral range is also described. This allows for the fast display of a lower resolution image such as a survey scan for OCT angiography, while processing of the higher resolution data is taking place.

In a further embodiment of the present invention, a purely software based solution to increase the A-scan rate for certain SS-OCT imaging modes is described. It does not require any changes to the SS-OCT hardware. The electronics, for example the detection bandwidth of the detector or the analog filters, do not have to be adjusted as the splitting of the spectra is done after the conversion to the digital data space and is part of the post-processing effort. This allows easy switching between fast imaging modes for overview scans or OCT Angiography and standard imaging modes. If the scan speed is increased based on the number of portions the data is divided, the field of view can be increased accordingly without a reduction in transverse sampling. Another advantage of splitting the spectra after digitization is that with a single acquisition, one obtains a high axial resolution/lower transverse sampling data set by not splitting the sweeps, while one can in parallel process the same data set with the proposed method to obtain a lower axial resolution/high transverse sampling data set for enface imaging modes. This enables the combination of a standard OCT scan with an angiography scan therefore reducing the examination time tremendously. It also allows for the generation of a fast survey or preview OCT angiography image before or while the data is processed to generate a higher resolution OCT angiography image either using a higher resolution data set and/or a more processing intensive OCT angiography technique.

DETAILED DESCRIPTION

Figure 1:
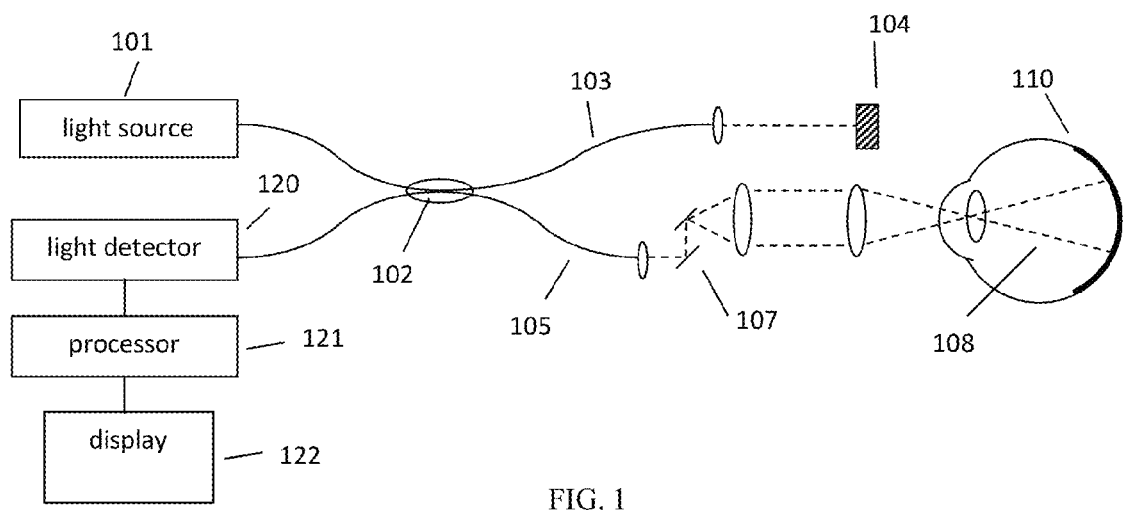
FIG. 1 illustrates a generalized OCT system for use in ophthalmology.

An optical coherence tomography scanner, illustrated in FIG. 1 typically includes a light source, 101. Two examples of suitable sources are a broadband light source with short temporal coherence length or a swept laser source. (See for example, Wojtkowski, et al., "Three-dimensional retinal imaging with high-speed ultrahigh-resolution optical coherence tomography," Ophthalmology 112(10):1734 2005 or Lee et al. "In vivo optical frequency domain imaging of human retina and choroid," Optics Express 14(10):4403 2006). Light from source 101 is routed, typically by optical fiber 105, to illuminate the sample 110, a typical sample being tissues at the back of the human eye. The light is scanned, typically with a scanner 107 or pair or scanning mirrors between the output of the fiber and the sample, so that the beam of light (dashed line 108) is scanned over the area or volume to be imaged. Light scattered from the sample is collected, typically into the same fiber 105 used to route the light for illumination. Reference light derived from the same source 101 travels a separate path, in this case involving fiber 103 and retro-reflector 104. Those skilled in the art recognize that a transmissive reference path can also be used. Collected sample light is combined with reference light, typically in a fiber coupler 102, to form light interference in a detector 120. The output from the detector is supplied to a processor 130. The results can be stored in the processor or displayed on display 140.

The interference causes the intensity of the interfered light to vary across the spectrum. For any scattering point in the sample, there will be a certain difference in the path length between light from the source and reflected from that point, and light from the source traveling the reference path. The interfered light has an intensity that is relatively high or low depending on whether the path length difference is an even or odd number of half-wavelengths, as these path length differences result in constructive or destructive interference respectively. Thus the intensity of the interfered light varies with wavelength in a way that reveals the path length difference; greater path length difference results in faster variation between constructive and destructive interference across the spectrum. The Fourier transform of the interference spectrum reveals the profile of scattering intensities at different path lengths, and therefore scattering as a function of depth in the sample (see for example Leitgeb et al, "Ultrahigh resolution Fourier domain optical coherence tomography," Optics Express 12(10):2156 2004). The profile of scattering as a function of depth is called an axial scan (A-scan). A set of A-scans measured at neighboring locations in the sample by transverse scanning produces a cross-sectional image (tomogram or B-scan) of the sample. A collection of B-scans creates a data volume or cube.

The range of wavelengths at which the interference is recorded (spectral range or bandwidth) determines the resolution with which one can determine the depth of the scattering centers, and thus the axial or depth resolution of the tomogram. Recording a limited range of optical frequencies results in a coarser axial resolution.

En face visualization techniques based on inter-frame change analysis (see for example US Patent Publication No.

2012/0277579 hereby incorporated by reference) require a high density of sampling points, and hence the time required to finish such scans can be significantly higher than compared to regular cube scans used in commercial OCT systems. As described above, for larger data volume acquisitions there are several major limitations:

1. Heavy post-processing times due to large data volumes make it difficult for the operator or doctor to perform and immediately review the scans or analysis.
2. Long acquisition times lead to the increased possibility and occurrences of eye motion. Eye motion can result in loss of data, image artifacts and hence greatly reduces the usability of the acquired data.
3. Critical pathologies can be missed as only smaller field of view (FOV) can be covered due to long acquisition times.

The axial resolution of a typical commercial OCT system is ~5-6 μm, whereas the lateral resolution is ~15-20 μm. In OCT angiography, the high axial resolution may not be very critical in improving the image quality of en face vasculature. This is because the majority of blood-flow contrast OCT techniques (Doppler OCT, phase contrast, phase variance, speckle variance, power of Doppler shift, normalized vector difference, ultrahigh sensitive optical microangiography (UHS-OMAG) etc.) have posterior shadow artifacts below the blood vessel, thereby effectively degrading the axial resolution for motion-contrast signals. Also, the most common visualization of the vasculature is the en face image that is obtained by summing or integrating the motion-contrast data in the axial direction. Hence, one of the solutions to improve the OCT angiography acquisition speeds and processing times without significantly affecting en face image quality could be to switch the OCT system to a lower axial resolution mode.

There are multiple ways in which acquisition and post-processing speeds can be improved and implemented for OCT angiography applications where the OCT angiography data in part or in its entirety can be collected or processed at a lower axial resolution before or while the data is being processed or collected to generate a higher resolution image. A few techniques will be described in detail below.

Reduced Axial Resolution Mode for High Speed Survey Scans

In a preferred embodiment of the present invention, a SS-OCT system can be operated in at least two different data acquisition modes. In the regular mode the full available spectral bandwidth of the system is used for typical OCT imaging (structural) and OCT angiography acquisition to obtain images at high axial resolution. In the second mode, the system can collect data at a lower axial resolution to be used for applications in the large FOV 'survey scans' by reducing the spectral sweep range of the swept source. Survey scans can be useful to detect pathologies over a larger FOV in shorter times. An alternative approach to obtain survey scans covering larger FOVs using unchanged axial resolution would be to use sparse spatial sampling densities to be able to finish the scans in the same amount of time. As far as the tradeoff between lateral sampling points and axial sampling points is concerned, it may be beneficial to increase the spatial sampling density at the cost of decreased axial resolution. For example, if the spectral sweep range is reduced by a factor of 4, the OCT angiography acquisition can be done 4 times faster, without significant overload in post-processing efforts and without any significant image on en-face vasculature image quality.

Figure 2:
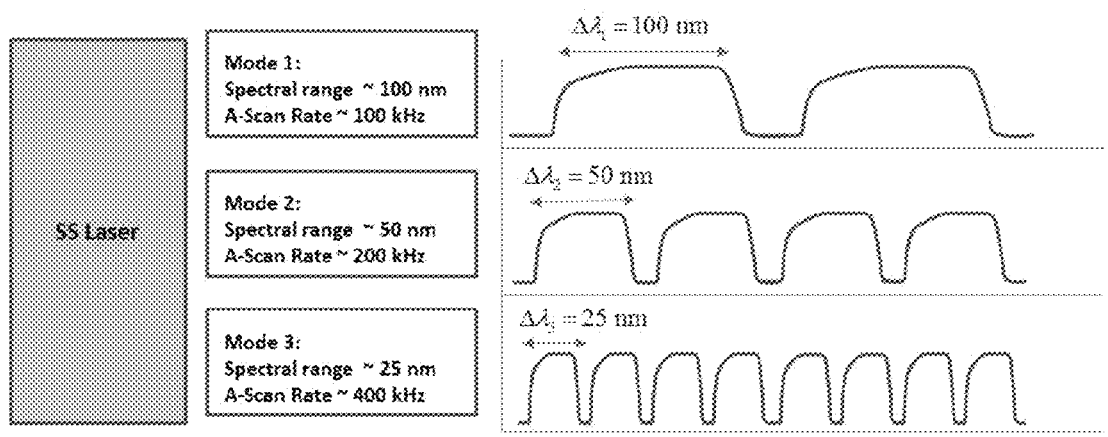
FIG. 2 illustrates a swept source OCT system capable of operating in three different axial resolution modes according to one embodiment of the present invention.

FIG. 2 shows a swept source capable of operating in up to 3 axial resolution modes at three different sweep rates. In the preferred embodiment, the swept source used in FIG. 2 has similar wavelength tuning rates across the three modes. The biggest advantage of this design is that there are almost no changes required in the detection system for different axial resolution modes. The approximate average sampling rates at the detector would remain approximately constant across all modes, both in the case of k-clock based acquisition or uniform temporal sampling. If the wavelength tuning rate and duty cycle are kept constant, the sweep rate will be inversely proportional to the spectral range. However, at the same time, the number of samples per sweep will decrease linearly with the decrease in axial resolution. It should be noted that the imaging depth remains largely unchanged across the different modes in this method if the tuning rate is not changed. Alternate implementations in which the tuning rate is not maintained constant also fall under the broad scope of this invention where a key idea is improve acquisition speed at the cost of axial resolution.

Although embodiments of the present invention are discussed herein with respect to SS-OCT systems for OCT Angiography, embodiments of the present invention are not limited to this configuration. One skilled in the art could imagine additional embodiments that would achieve these goals falling within the scope of the invention. One example of the additional embodiments that fall within the scope of this invention is use of variable resolution spectral domain OCT with changeable acquisition speeds. Several of the ideas discussed in the patent application US 2010/0110376 can be used to implement variable resolution SD-OCT systems for applications in OCT angiography according to the present invention.

Faster Analysis for Image Previews after Acquisition

One of the major workflow challenges for OCT scans that require long acquisition and post-processing times is the significant time delays required for display of processed images and results to ensure that the scan was obtained successfully. Due to the large data sizes and heavy post-processing efforts, OCT angiography scan analysis could have significant delays and it will be challenging for the machine operator to decide if the scan needs to be reacquired. Hence in another embodiment of the present invention, we propose using a selected portion of the spectrum for faster analysis to rapidly generate OCT angiography images for en face vasculature visualization. In this case, the full wavelength range of the source would be used to collect data, but only a selected portion would be initially processed for image preview purposes. A quicker analysis can help the operator to decide if the data acquisition was done right to avoid the possibility of needing to perform repeat measurements later. Analysis and processing using the full axial resolution can be done later for better results and diagnosis or for different types of analysis. The rapid generation of en face images over larger FOV can also aid the operator to select specific regions of interesting pathology and perform more dense scans in the region of interest. It must be noted that this is simply a post-processing method which doesn't impact acquisition speeds but aids in quicker display of analysis to enable workflow related real-time decisions after the scan acquisition.

Figure 3:
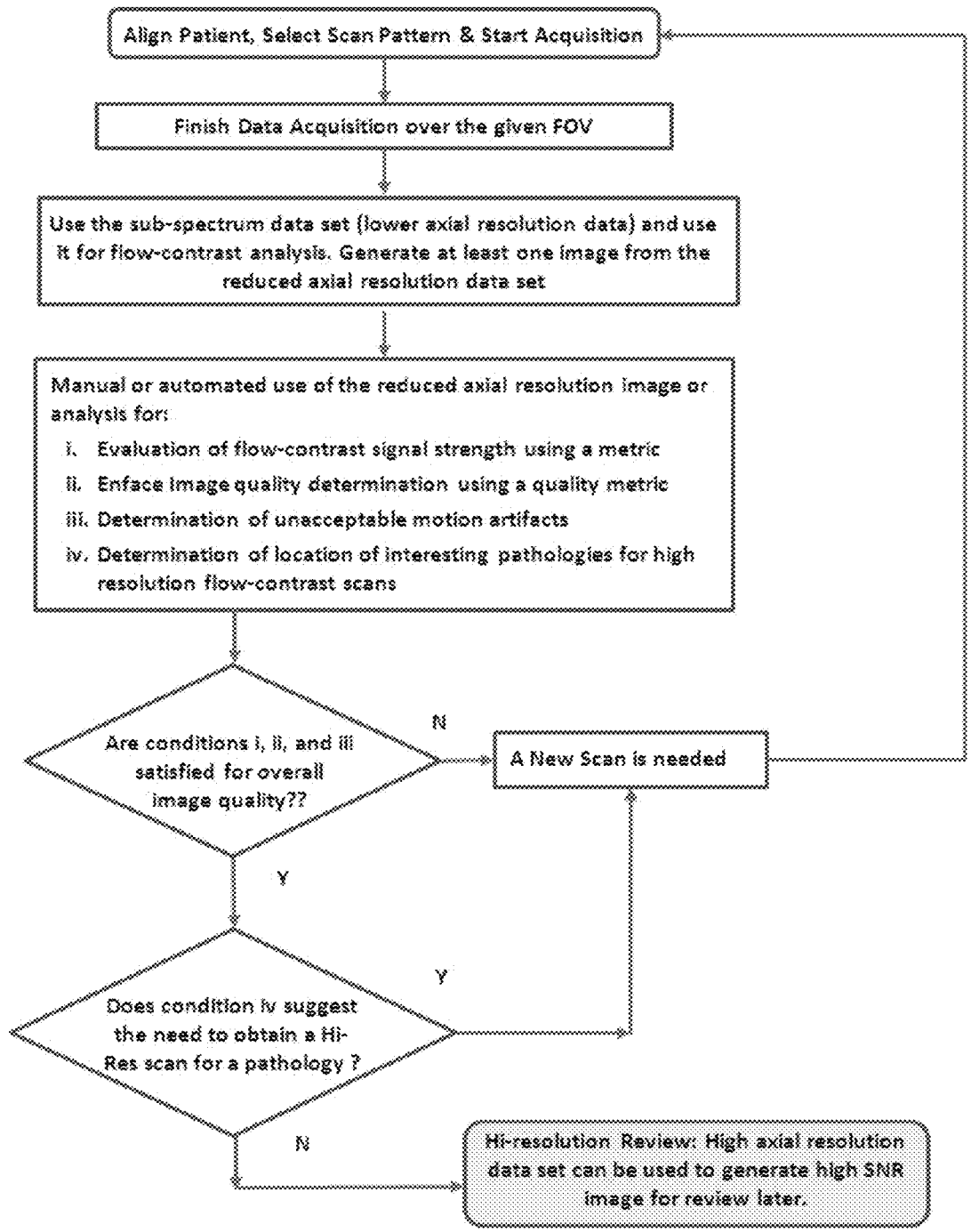
FIG. 3 illustrates a workflow diagram that could be used to collect and evaluate OCT data according to an embodiment of the present invention.

FIG. 3 shows a flowchart depicting various steps in one of the preferred embodiments of the present invention. After the OCT angiography data is acquired, the overall data sizes can be significantly reduced by using only a smaller portion of the spectrum or sub-spectrum corresponding to each A-scan measurement. The modified 3D volume with sub-spectrum information has reduced size and it can be used to generate OCT angiography analysis, albeit with data that supports lower axial resolution. Here we exploit the fact that loss of axial resolution does not significantly degrade the en-face vasculature images. However, it must be noted that there will be some degradation in the images compared to those obtained from full-spectrum original volume data as the sub-spectrum data will have a lower signal to noise ratio (SNR). Nonetheless, the trade-off will still be beneficial as it may reduce the processing time. At this stage, the operator could either visually inspect the low axial resolution OCT angiography images to decide if the scan is of acceptable quality and it doesn't have any unacceptable motion artifact. In order to assist the operator, a quality metric could also be generated that can be used to assess the image quality and a decision can be made whether the scan needs to be repeated. Further, the operator could use the preview image to identify regions of pathology and obtain a higher resolution, smaller FOV scan in the region of interest. While this lower axial resolution data facilitates faster processing and viewing of images, the complete spectral data-set can be used to generate improved quality images later. This method could also be combined by sub-sampling of lateral points from the acquisition volume.

There have been a variety of techniques for visualization of vasculature using OCT including different phase and/or intensity based techniques to map blood flow such as phase-contrast, Doppler, speckle variance, intensity variance, amplitude decorrelation, etc. The scope of this invention covers any OCT based method that is used for generation of flow-contrast or motion-contrast based OCT analysis. It should be noted that phase sensitive methods commonly require a phase correction in order to compensate for phase shifts introduced by sample movement. The phase correction usually adds to the processing time. In order to minimize wait times between the acquisition of the data set and the display of a capillary contrast image obtained by a phase sensitive method, a portion or all of the data set can be processed first using an intensity motion contrast technique. This can allow presenting a slightly lower quality image as a first overview or preview, while the high definition phase contrast image is being processed. In a preferred embodiment, the processing with the second technique requires at least 1.5 times more processing time than the first technique. Also, the intensity based OCT angiography methods can be used in combination with the invention above to further reduce the post-processing times and allow operators to make quicker decisions. This is of course an option not only available for invention described herein, but is also applicable for any SS-OCT or SD-OCT acquisitions.

Sweep Rate Multiplication

In a further embodiment of the invention, each sweep of the laser is split into N parts either during acquisition or in post-processing. This results in a factor of N more A-scans. In a preferred embodiment, this can be done while increasing the transverse scan rate at the same time by the same factor N, resulting in a data set with a factor of N larger field of view, while the original transverse spacing between samples is maintained. While the number of transverse samples is increased by the factor N, the axial resolution of each resulting A-scan is reduced by the same factor N. For certain imaging modes this is negligible (e.g. OCT Angiography methods, photoreceptor imaging, fundus projections) or tolerable (e.g. fast SS-OCT extreme wide field overview scans). This method is only realizable because in SS-OCT the spectral density function S(k) is not acquired instantaneously as in spectrometer based SD-OCT, but as a function of time. By splitting a single sweep into multiple parts, one receives multiple sweeps with smaller spectral bandwidths but shorter sweep periods, which are just as regular sweeps acquired successively in time. The reduced sweep period and consequently increased sweep rate, ultimately leads to a reduction in imaging time. This time may be used to increase the transverse sampling or to increase the field of view. In contrast to standard sweeps, the resulting split sweeps exhibit different spectral bands, which may introduce a small axial shift of the resulting A-scan after the Fourier transform (FFT). This shift is in most cases however smaller than the resulting axial resolution and is therefore negligible. Splitting the sweep corresponds also to a splitting of the signal intensities, resulting in a factor N lower sensitivity for each resulting A-scan. This however applies to the same extent for every method of increasing the A-scan rate, while maintaining the optical power of the light source at the same level. If the maximum exposure is not limited by laser safety, the optical output power of the light source may be increased to compensate for this signal loss.

Figure 4:
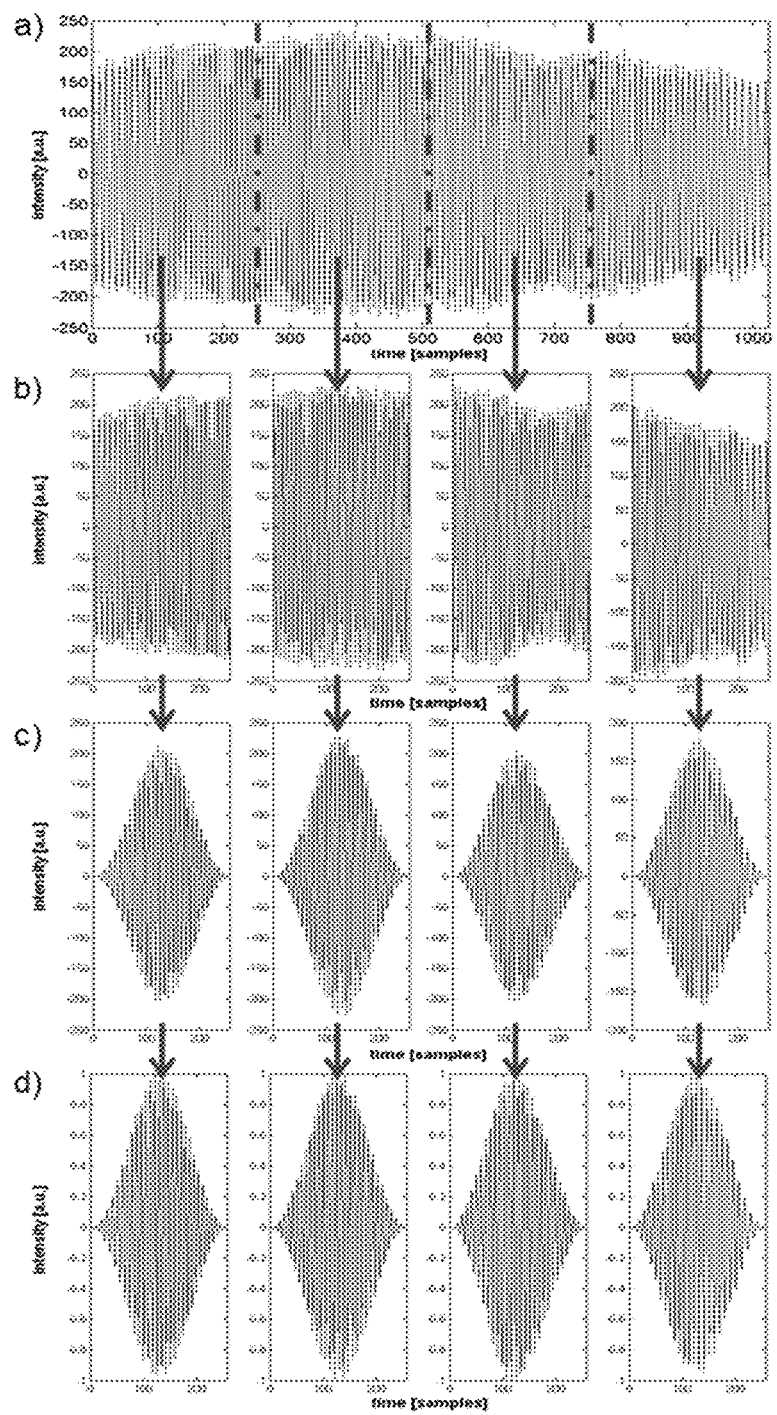
FIG. 4 illustrates how an OCT data set could be broken into four parts for separate processing according to an embodiment of the invention.

In one preferred embodiment of the invention illustrated in FIG. 4, the following steps can be taken to achieve a sweep rate multiplication through splitting of the spectral sweep:

1. Collect SS-OCT data with a factor N times faster transverse scanning.
2. Perform dispersion correction and resampling with respect to k on each full wavelength sweep as shown in FIG. 4(a).
3. Subtract the background from the full sweeps.
4. Split each sweep by a factor N as shown in FIG. 4(b) where N=4.
5. Shape the resulting split sweeps by multiplying them with a windowing function, e.g. a Hann window (FIG. 4(c)). Shaping each split sweep separately reduces the influence of different spectral power for different parts of the full sweep. The spectral shaping also, as in standard OCT, improves the shape of the axial point spread function after the FFT.
6. Normalize the intensities of the split sweeps (FIG. 4(d)). As the full sweep most likely shows different spectral power for different parts of the sweep, the resulting split sweep will exhibit different intensities as well. This consequently leads to varying intensities of the resulting A-scans within a B-scan. Normalizing the intensities will overcome this problem and produce B-scans with homogenous intensity distributions.
7. Perform the FFT along k for each of the split sweeps separately.
8. Shift the resulting A-scans axially to compensate for their relative difference in central wavelength. This shift is however most likely so small that it only corresponds to a subpixel shift of the A-scan. Therefore this step may be negligible in most cases and not cause any image degradation.

Figure 5:
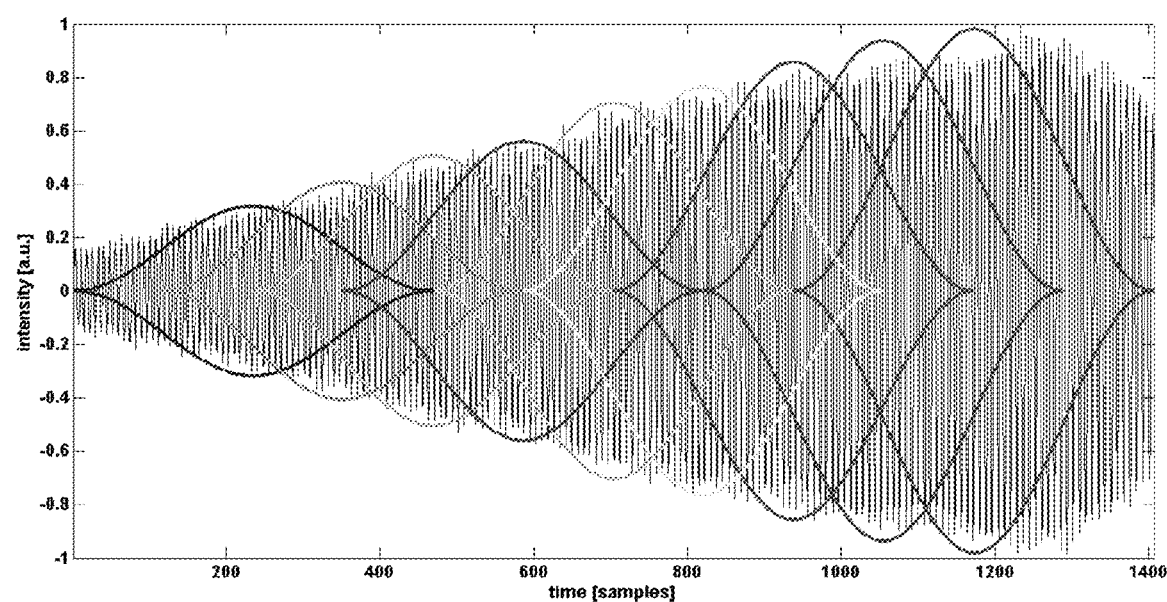
FIG. 5 illustrates an alternative approach to breaking up an OCT data set into subsets for processing according to an embodiment of the present invention.

For the case of FIG. 4 where the sweep is split into four different portions for processing, the transverse scan speed would be increased by a factor of 4. This would mean that the transverse position of the probing spot at the beginning of the sweep will differ from the transverse position of the probing spot at the end of the sweep, resulting in 4 spatially adjacent A-scans. The method could also be applied without increased scan speed. In this case the field of view would be maintained, while the transverse sampling would be increased. The sweep can also be split during acquisition by increasing the number of trigger signals during a single sweep of the laser. In the above described embodiment, one sacrifices some signal intensity by the spectral shaping of the split sweeps. However, splitting of a spectral sweep can also be done in a way that there is partial spectral overlap between adjacent split sweeps as illustrated in FIG. 5. This avoids losing signal intensity due to the individual spectral shaping of the split sweeps and therefore maximizes the use of the interference signal.

If the sweep is split into sub-sweeps with equal spectral range, the axial resolution of the individual sub sweeps will differ slightly due to their different central wavelengths. In an alternate implementation of the invention, the N sub-spectrums may be split non-uniformly in wavelength ranges to maintain similar axial resolution across different sub-spectrums. This might however only be interesting when using large spectral sweep ranges, where the difference in central wavelength between the sub-sweeps becomes significant.

The proposed method will produce the best results using swept sources with high sweep duty cycles. This is because the transverse scanner is operated at a higher speed, which means that also during the "off-time" of the swept source the scanner travels a longer distance than in the regular imaging mode, creating larger un-sampled gaps in the B-scans. These gaps can be minimized by using swept sources with a sweep duty cycle close to 100%. Alternatively one could drive the scanner with a "step-function", where the scanner is stopped during the off-times of the swept laser source. This is however, at least for fast systems, usually not realizable due to the relatively long response times of the scanners.

After the FFT, a complex valued signal is obtained which allows further processing of its amplitude and phase just as in conventional SS-OCT.

A data set which is used to multiply the sweep rate using the presently described invention can always be used for standard OCT signal processing without splitting. The same is true the other way around: a standard SS-OCT data set can be used for the method described herein. This allows encoding a high transverse sampling scan into a standard scan (e.g. a retina data set acquired using a relatively low transverse resolution scan pattern commonly used in commercial systems to acquire the structural information). The described invention can be applied to the same acquisition, resulting in a data set with a high transverse sampling but lower axial resolution, which can then be used for example in OCT Angiography techniques.

Besides the applications in OCT Angiography methods, the present invention may also prove advantageous for other imaging schemes, where high transverse sampling is required to support the transverse resolution, while the axial resolution may not be of large importance. This is the case for photoreceptor imaging using a SS-OCT system. In this case the maximum acquisition time is limited, as one requires quasi motion artifact-free volumes to comprehensively resolve the cone photoreceptor mosaic. At the same time, a large transverse sampling is required to support the high transverse resolution. This significantly limits the field of view of such acquisitions. Splitting the sweeps and therefore increasing the lateral sampling may enable imaging of larger areas with high transverse resolution. Since one is mostly interested in the enface projection of the cone mosaic, the reduced axial resolution may not play an important role.

Although the description of the present invention is discussed herein mostly with respect to the sample being a human eye, applications of this invention are not limited to eye and can be applied to any application using SS-OCT. Although various applications and embodiments that incorporate the teachings of the present invention have been shown and described in detail herein, those skilled in the art can readily devise other varied embodiments that still incorporate these teachings.

The following references are hereby incorporated by reference:

PATENT DOCUMENTS

U.S. Pat. No. 7,864,335 Terakawa et al. "Method, Apparatus, and Program for Processing Tomographic images, and optical tomography system:
U.S. Pat. No. 7,375,818 Kawahara "Optical tomography system"
U.S. Pat. No. 7,692,797 Kawahara "Optical tomography system"
U.S. Pat. No. 6,549,801 Chen et al. "Phase-resolved optical coherence tomography and optical doppler tomography for imaging fluid flow in tissue with fast scanning speed and high velocity sensitivity"
U.S. Pat. No. 7,359,062 Chen et al. "High speed spectral domain functional optical coherence tomography and optical Doppler tomography for in vivo blood flow dynamics and tissue structure"
U.S. Pat. No. 7,995,814 Fingler et al. "Dynamic motion contrast and transverse flow estimation using optical coherence tomography"
US Patent Publication No. 2012/0277579 "Inter-frame Complex Data Analysis Techniques"
US Patent Publication No. 2010/0110376 Everett et al., "Variable resolution OCT scanner and method for using the same,"
U.S. patent application Ser. No. 13/354,066 "Method, Systems and Applications of Variable Imaging Depth in Fourier Domain Optical Coherence Tomography" filed Jan. 24, 2012
PCT Publication No. WO 2010/006785 Hacker et al "Optical coherence tomography methods and systems"

NON-PATENT LITERATURE

An et al., "In vivo volumetric imaging of vascular perfusion within human retina and choroids with optical microangiography," Optics Express 16, 11438-11452 (2008).
Fingler et al. "Mobility and transverse flow visualization using phase variance contrast with SD-OCT," Optics Express 15, 12636-12653 (2007).
Fingler et al. "Volumetric microvascular imaging of human retina using OCT with a novel motion contrast technique," Optics Express 17, 22190-22200 (2009).
Jia et al. "Split-spectrum amplitude-decorrelation angiography with OCT," 20, 4710-4725 (2012).
Klein et al. "The effect of micro-saccades on the image quality of ultrawide-field multimegahertz OCT data," SPIE Photonices West 2012, Paper #8209-13 (2012).
Blatter, T. Klein, B. Grajciar, T. Schmoll, W. Wieser, R. Andre, R. Huber, and R. A. Leitgeb, "Ultrahigh-speed non-invasive widefield angiography," J. Biomed. Opt. 17, 070505 (2012).
Kim et al. "In vivo volumetric imaging of human retinal circulation with phase-variance OCT," Biomedical Optical Express, 2, 1504-1513 (2011).
Leitgeb et al, "Ultrahigh resolution Fourier domain optical coherence tomography," Optics Express 12(10):2156 (2004).
Makita et al. "Optical Coherence Angiography," Optics Express 14, 7821-7840 (2006).
Mariampillai et al. "Optimized speckle variance OCT imaging of microvasculature," Optics Letters 35, 1257-1259 (2010).

Podoleanu et al. "OCT en-face images from the retina with adjustable depth resolution in real time" IEEE Journal of Selected Topics in Quantum Electronics 5(4); 1176-1184 (1999).

Lee et al. "In vivo optical frequency domain imaging of human retina and choroid," Optics Express 14(10):4403 (2006).

Wang et al. "Three dimensional optical angiography," Optics Express 15, 4083-4097 (2007).

Wojtkowski, et al., "Three-dimensional retinal imaging with high-speed ultrahigh-resolution optical coherence tomography," Ophthalmology 112(10):1734 (2005).

Xi et al "Generic real-time uniform K-space sampling method for high-speed swept-source optical coherence tomography," Optics Express 18(9):9511 (2010).

Yali et al. "Split-spectrum amplitude-decorrelation angiography with optical coherence tomography," Opt. Express 20, 4710-4725 (2012).

Zhang et al "Swept laser source at 1 um for Fourier domain optical coherence tomography," Applied Physics Letters 89, 073901 (2006).

The invention claimed is:

1. A method of analyzing the eye of a patient using a swept source optical coherence tomography (OCT) system, said method comprising:

collecting a series of OCT data over a series of transverse locations in the eye, wherein the data is collected at two different axial resolutions, wherein the OCT system includes detection electronics and wherein the detection electronics remain unchanged as the axial resolution is adjusted;

processing a first portion of the data to determine motion contrast wherein the first portion of the data was collected at the lower axial resolution;

processing a second portion of the data to generate a structural image, wherein the second portion of the data was collected at a higher axial resolution wherein the two different axial resolutions are achieved by switching the swept source between at least two spectral tuning ranges and sweep rates, where the higher sweep rate corresponds to a shorter spectral tuning range;

generating an en face vascular image with the first portion of the processed data; and storing or displaying the second portion of the processed data.

2. A method as recited in claim 1, wherein the OCT data is collected using a spectral domain OCT system.

3. A method as recited in claim 1, wherein the processing of the second portion of data occurs after the processing of the first portion.

4. A swept-source optical coherence tomography (SS-OCT) system generating images of the eye comprising:

a light source for generating a probe beam wherein said source is swept in wavelength over a spectral range at a sweep rate;

optics for scanning the beam over a set of transverse locations across the eye during a wavelength sweep of the laser;

a detector for measuring light returned from the eye as a function of wavelength that acquires data at a data acquisition rate; and a processor for performing Fourier transformations and generating images of the eye based on the output of the detector over a sampling of wavelengths, wherein the data for each sweep of the spectral range is divided into multiple subsets of data of different spectral ranges prior to Fourier transformation and image generation, wherein the multiple subsets contain data from different transverse locations on the eye; and a display for displaying the processed image or images.

5. A SS-OCT system as recited in claim 4, wherein the transverse scanning speed is increased based on the number of subsets the data is divided into.

6. A SS-OCT system as recited in claim 4, wherein said processor also Fourier transforms and generates image data without dividing the data into subsets.

7. A SS-OCT system as recited in claim 4, wherein the generated image is a motion sensitive image.

8. A SS-OCT system as recited in claim 7, wherein the image is one of Doppler OCT, phase contrast, power of Doppler shift, phase variance, speckle variance, normalized vector difference, ultrahigh sensitive optical microangiography.

9. A SS-OCT system as recited in claim 4, wherein the photoreceptors in the eye are imaged.

10. A SS-OCT systems as recited in claim 4, wherein the anterior segment of the eye is imaged and biometry measurements are made.

11. A SS-OCT system as recited in claim 4, wherein the subsets of data of different spectral ranges contain overlapping wavelengths.

12. A SS-OCT system as recited in claim 4, wherein the subsets of data of different spectral ranges contain non-overlapping wavelengths.

13. A method of analyzing the eye of a patient using an optical coherence tomography (OCT) system, said method comprising:

collecting a series of OCT data over a series of transverse locations in the eye, wherein the data includes both intensity and phase, processing a first portion of the data using an intensity motion contrast technique to determine motion contrast and generating a first, preview image corresponding thereto; and processing a second portion of the data using a phase sensitive motion contrast technique to determine motion contrast and generating a second image corresponding thereto, wherein the processing of the second portion of the data takes more processing time than processing the first portion of the data and wherein the second image is of higher quality than the first image.

14. A method as recited in claim 13, wherein the first image is displayed before or while the second portion of the data is processed.

15. A method as recited in claim 13 wherein the first and second portion of data cover the same spectral range.

16. A method as recited in claim 13, wherein the step of processing the first portion of the data is performed using speckle variance, and the step of processing the second portion of the data is one of: Doppler OCT, phase contrast, power of Doppler shift, phase variance, normalized vector difference, and ultrahigh sensitive optical microangiography.

17. A method as recited in claim 13, wherein the step of processing the second portion of the data takes at least 1.5 times more processing time than the step of processing the first portion of the data.

* * * * *